(12) United States Patent
Smith

(10) Patent No.: US 7,786,081 B2
(45) Date of Patent: Aug. 31, 2010

(54) PEPTIDE COMPOSITION

(75) Inventor: John Arthur Smith, Liverpool (GB)

(73) Assignee: Pepsyn Ltd., Liverpool (GB)

( * ) Notice: Subject to any disclaimer, the term of this patent is extended or adjusted under 35 U.S.C. 154(b) by 0 days.

(21) Appl. No.: 11/502,345

(22) Filed: Aug. 9, 2006

(65) Prior Publication Data

US 2007/0160558 A1  Jul. 12, 2007

Related U.S. Application Data

(63) Continuation of application No. 10/512,512, filed as application No. PCT/GB03/01439 on Apr. 2, 1993, now abandoned.

(30) Foreign Application Priority Data

Apr. 24, 2002 (GB) ................................. 0209384.7

(51) Int. Cl.
 A61K 38/16 (2006.01)
 A61K 38/10 (2006.01)
 A61K 8/64 (2006.01)

(52) U.S. Cl. ............................ 514/12; 514/13; 514/14; 514/15; 530/300; 424/9.1

(58) Field of Classification Search .................. 514/12, 514/13, 14, 15; 530/300; 424/9.1
 See application file for complete search history.

(56) References Cited

U.S. PATENT DOCUMENTS

| 3,558,770 A | 1/1971 | Gordon et al. |
| 5,284,827 A | 2/1994 | Maione et al. |
| 5,427,769 A | 6/1995 | Berrocal et al. |
| 5,965,536 A | 10/1999 | Cohen et al. |
| 6,462,171 B1 * | 10/2002 | Soto-Jara et al. ............. 530/326 |
| 6,506,732 B1 | 1/2003 | Amiot |

FOREIGN PATENT DOCUMENTS

| EP | 0 457 565 | 11/1991 |
| JP | 3255095 | 11/1991 |
| JP | 6211689 | 8/1994 |
| WO | WO 92/00994 | 1/1992 |
| WO | WO92/15279 | 9/1992 |
| WO | WO 95/29933 | 11/1995 |
| WO | WO 96/34614 | 11/1996 |
| WO | WO 97/16460 | 5/1997 |
| WO | WO 98/52524 | 11/1998 |
| WO | WO 00/06108 | 2/2000 |
| WO | WO 02/02133 | 1/2002 |
| WO | PCT/GB03/01439 | 9/2003 |

OTHER PUBLICATIONS

Stem, 2004, "Treatment of Photoaging," *N. Engl. J. Med.* 350(15):1526-1534.
Watson et al., 2001, "A Short-Term Screening Protocol, Using Fibrillin-1 as a Reporter Molecule, for Photoaging Repair Agents," *J. Invest. Dermatol.* 116(5):672-678.
Watson et al., 1999, "Fibrillin-Rich Microfibrils are Reduced in Photoaged Skin. Distribution at the Dermal-Epidermal Junction," *J. Invest. Dermatol.* 112(5):782-787.
Dunn et al., 1997, Does Estrogen Prevent Skin Aging? Results from the First National Health and Nutrition Examination Survey (NHANES I), *Archives of Dermatology*,133(3):1-3 (3-page Abstract).
Poulsen et al., 1997, "Factors Affecting IL-1-Mediated Collagen Metabolism by Fibroblasts and the Pathogenesis of Periodontal Disease: A Review of the Literature," *Crit. Rev. Oral Biol. Med.* 8(2):217-236.
Liu et al., "A Growth Factor Activity in Bovine Milk", Biochemical Society Transactions, 1996, p. 342S, vol. 24, No. 3, Colchester, Essex, GB.
Matsui et al., Absorption of Val-Tyr with in Vitro Angiotensis I-Converting Enzyme Inhibitory Activity into the Circulating Blood System of Mild Hypertensive Subjects, Biol. Pharm. Bull., 2002, pp. 1228-1230, vol. 25, No. 9.
Yokyama et al., Peptide Inhibitors for Angiotensin I-Converting Enzyme from Thermolysin Digest of Dried Bonito, Biosci. Biotech. Biochem., 1992, pp. 1541-1545, vol. 56, No. 10.

\* cited by examiner

*Primary Examiner*—Chih-Min Kam
(74) *Attorney, Agent, or Firm*—Joseph R. Baker, Jr.; Gavrilovich Dodd & Lindsey LLP

(57) ABSTRACT

Provided is use of a peptide, or a derivative of a peptide, in the manufacture of a medicament effective in stimulating fibroblasts to produce fibrillin, wherein the peptide comprises an amino acid sequence present in an α-S2 casein precursor, said sequence comprising 3 or more amino acids, and not comprising at its N-terminal amino acid of the full α-S2 casein precursor. Further provided is use of a peptide, or a derivative of a peptide, in the manufacture of a medicament effective in stimulating fibroblasts to produce fibrillin, wherein the peptide has an α-S2 casein fragment activity.

13 Claims, 5 Drawing Sheets

Typical CM52 run

Typical Butyl Sepharose run

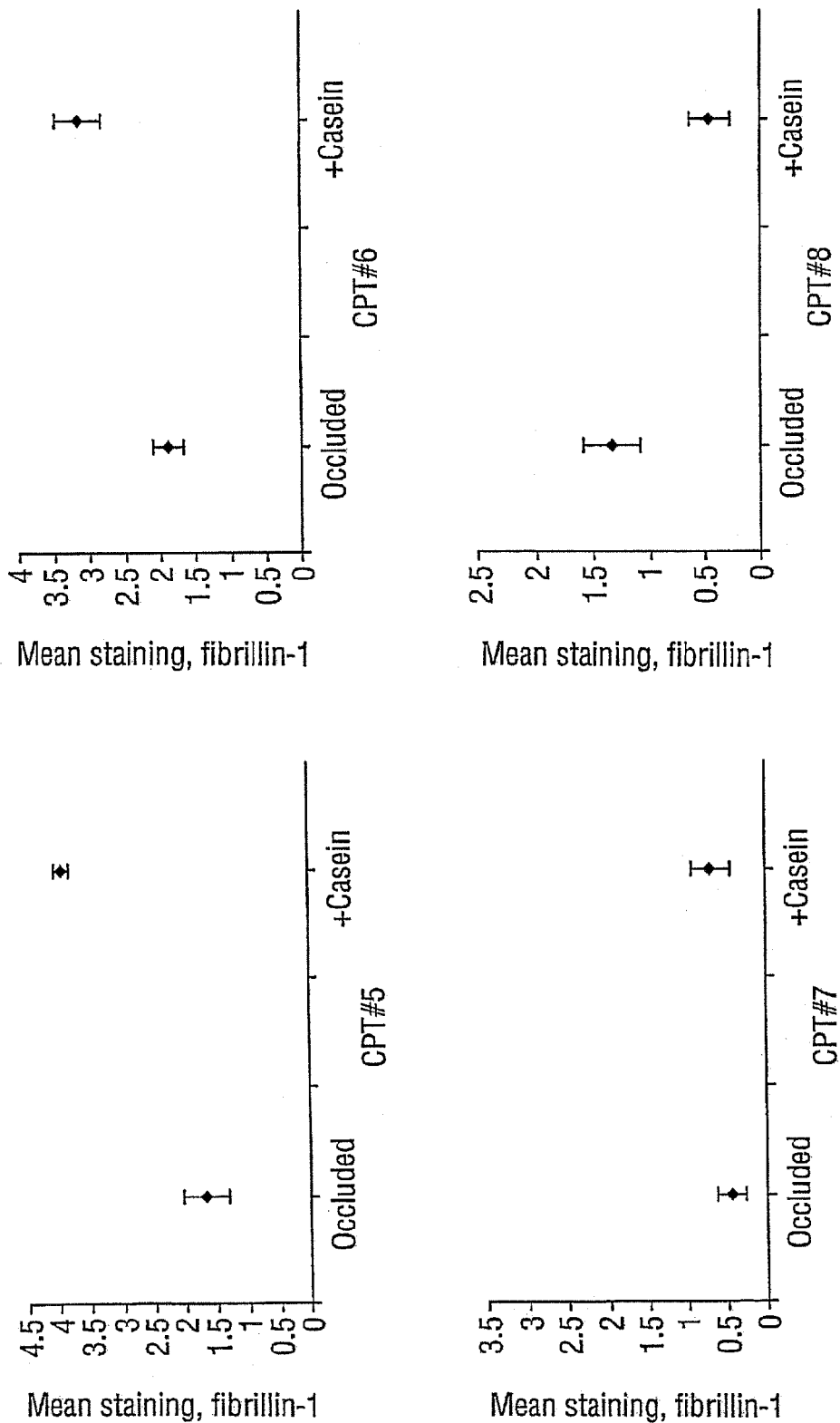

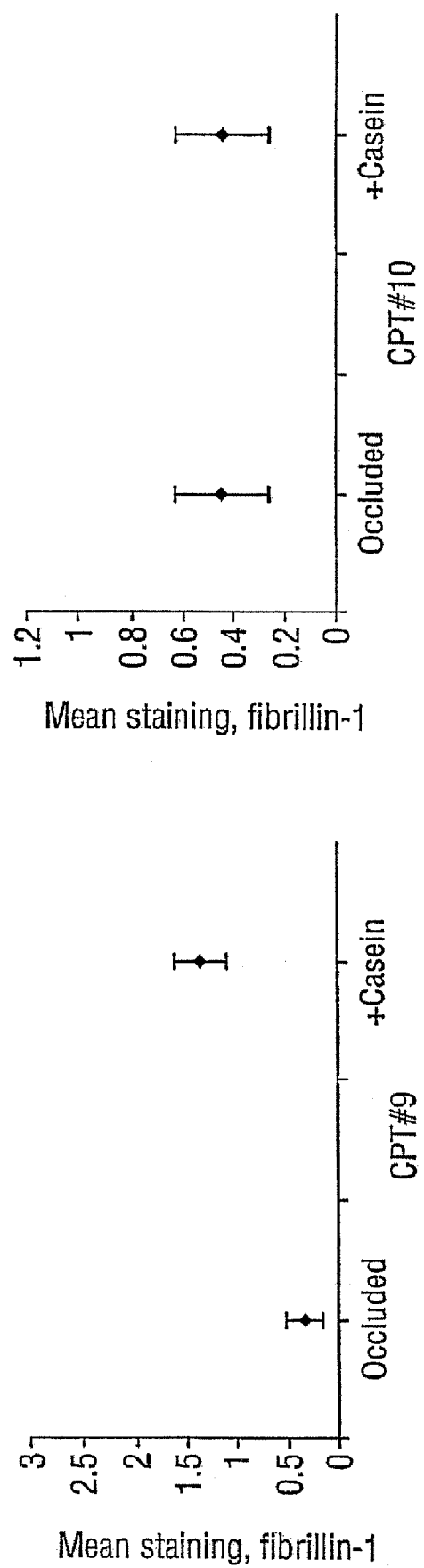

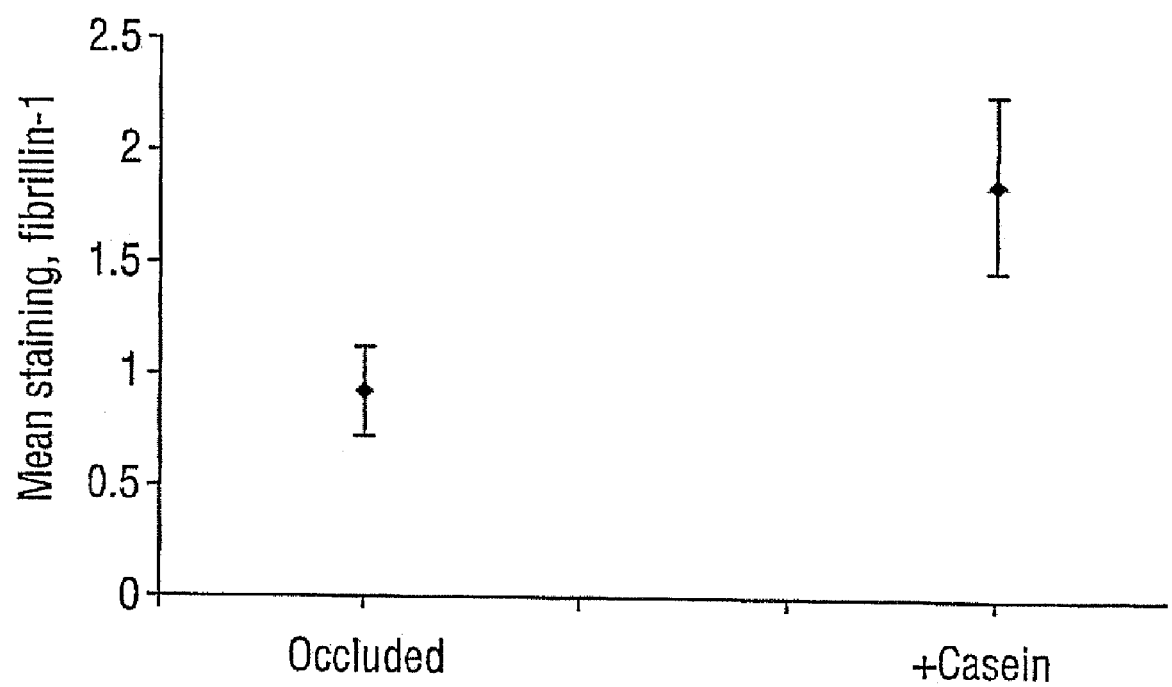

PEPTIDE COMPOSITION

1. CROSS REFERENCE TO RELATED APPLICATION

This application is a continuation of application Ser. No. 10/512,512 filed Jul. 7, 2005, now abandoned, the contents of which are incorporated herein by reference. Application Ser. No. 10/512,512 is a national stage application filed under 35 U.S.C. §371 of international application No. PCT/GB03/01439, filed Apr. 2, 2003, which in turn claims priority to GB0209384.7 filed Apr. 24, 2002. Benefit under 35 U.S.C. §120 to application Ser. No. 10/512,512 and priority under 35 U.S.C. §365 to international application No. PCT/GB03/01439 and GB0209384.7 is claimed.

2. BACKGROUND

The present invention relates to a protein, a peptide (generally a polypeptide), a peptide derivative, or peptide fragment which can be used to alleviate or prevent an effect of aging, particularly an effect of aging in skin, by stimulating the production of fibrillin in fibroblasts. This may be in a method of treatment or a cosmetic method. The invention also relates to the same peptides, polypeptides, peptide derivatives or peptide fragments which can be used as a prophylactic or treatment for periodontal diseases (gum diseases) by stimulating the production of fibrillin in fibroblasts. This may be in a medical method of treatment if desired. In particular the invention relates to use of a peptide which comprises an amino acid sequence from an α-S2 casein precursor.

For many years it has been known that, in addition to its nutritional content, milk contains growth promoting activity for cells. In this connection, epidermal growth factor (EGF) has been identified in human (Shing and Klagsbrun, 1984; Petrides, 1985), rat (Raaberg et al., 1990), swine (Tan et al., 1990) and goat (Brown and Blakeley, 1983) milk.

The EGF present in rat milk has been shown to be significant for the normal development of rat pups (Oka et al, 1983). EGF has not, however, been found in bovine milk (Read 1985). Instead, insulin-like growth factor (IGF) I and II (Francis et al., 1986) and bovine colostrum growth factor (BCGF), which is structurally related to Platelet-derived Growth Factor (PDGF) (Shing and Klagsbrun, 1984; Brown and Blakeley, 1994), have been identified in bovine milk.

In published International Application WO 97/16460 it is disclosed that bovine milk contains growth promoting activity for a rat mammary fibroblast cell line (Rama 27), which is not significantly stimulated by IGF or PDGF. In this application peptide sequences are identified which elicit this growth promoting activity. These sequences are identified as sequences that are substantially identical to the C-terminal end of bovine α-S2 casein precursor. The application indicates that these peptides or salts thereof may be used for the manufacture of medicaments or foodstuffs for promoting growth.

Published European Patent Application EP 0 457 565 discloses milk protein hydrolysate and compositions for use in hair and skin treatment. The proteins in the hydrolysate are not specifically defined and have molecular weights of less than 1000 daltons. These are thus very small hydrolysis products from a wide variety of proteins present in milk.

Published PCT Applications WO 92/00994, WO 95/29933 and WO 96/34614 disclose extracts from milk which may be used as growth promoting agents and agents for treating alimentary tract damage. The milk product extract may be from human or animal milk and includes cheese whey extracts and skim-milk extracts. The documents imply that IGF I or II are active ingredients giving the products their utility, and do not indicate that the products should comprise any specific protein.

In addition, topical applications, such as creams, have been marketed that claim anti-aging efficacy for added Epidermal Growth Factor (EGF) (Estee Lauder, advertised in Elle, 1999) and for 'whey proteins' (Estee Lauder's 'Diminish' in Martha Stewart's Living, February, 2000). However, this efficacy has not been shown to be especially high.

In published international application WO 02/02133, a composition for treating periodontal disease and signs of aging in skin is disclosed. This composition employs an α-S2 casein precursor capable of stimulating the production of collagen in fibroblasts.

3. SUMMARY

It is an object of the present invention to solve the problems associated with the prior art. In particular, it is an object of the present invention to provide an agent capable of alleviating or preventing the effects of aging in skin. It is also an object of the invention to provide an agent capable of treating or preventing periodontal disease. Surprisingly, the inventors have found that an α-S2 casein precursor and related species, such as those disclosed as growth promoters in WO 97/16460, are extremely useful in alleviating and preventing the effects of aging in skin, and in treating periodontal disease, by stimulating the production of fibrillin in fibroblasts. The α-S2 casein precursor and precursor fragments and derivatives used in the present invention are superior to known anti-aging products and products used for treating gum disease, and in particular to the agents disclosed in the above prior art.

Accordingly, the present invention provides use of a peptide, or a derivative of a peptide, in the manufacture of a medicament effective in stimulating fibroblasts to produce fibrillin, wherein the peptide comprises an amino acid sequence present in an α-S2 casein precursor, said sequence comprising 3 or more amino acids, and not comprising at its N-terminus the N-terminal amino acid of the full α-S2 casein precursor. The invention also provides use of a peptide, or a derivative of a peptide, in the manufacture of a medicament effective in stimulating fibroblasts to produce fibrillin, wherein the peptide has an α-S2 casein fragment activity. The medicament is effective in alleviating or preventing periodontal disease and/or in alleviating or preventing an effect of aging in skin, preferably an effect of photoaging (damage or aging caused by exposure or overexposure to UV light or sunlight).

The above-defined uses of the present invention include use of the peptide, or its derivative, either in a pure form, or in a partially purified form, such as that obtainable by isolation of the peptide from a natural source. Thus, the present use may extend to employment of the peptide in its natural unpurified form, such as using a natural substance that comprises the peptide or its derivative, or may involve use of the peptide or its derivative in any level of purification, including entirely (100%) pure. The peptide may also be from a proteolytic digest or a non-natural source, such as a synthetic peptide. In the context of this invention, the term peptide is intended to include proteins, polypeptides and peptide fragments.

The present invention may be employed in a cosmetic and/or medicinal method for alleviating or preventing an effect of aging in skin, which method comprises treating a subject with a polypeptide, or a derivative of a polypeptide, wherein the polypeptide comprises an amino acid sequence present in an α-S2 casein precursor, said sequence comprising 3 or more amino acids, and not comprising the N-terminus of the full α-S2 casein precursor.

To reiterate, the present inventors have surprisingly found that a peptide comprising an amino acid sequence from an α-S2 casein precursor, and in particular a fragment of such a peptide, has a very beneficial effect upon the skin, preventing and alleviating many effects of aging, and treating and preventing periodontal disease. The effect of these particular agents is superior to the effect of prior art agents. By fragments, in the context of the present invention it is meant any part of a sequence from a protein, polypeptide or peptide that is not the full sequence.

4. BRIEF DESCRIPTION OF THE FIGURES

The invention will be further described by way of example only with reference to the following drawings and specific embodiments, in which:

FIG. 4 shows a corresponding pooled analysis of this study.

5. DETAILED DESCRIPTION

Figure 1:
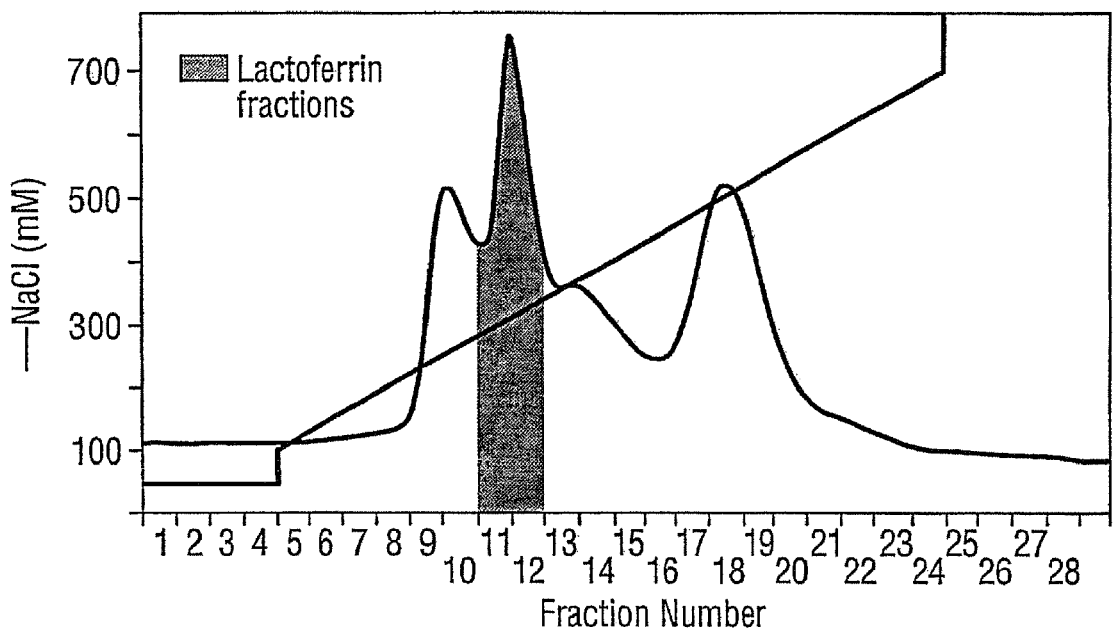
FIG. 1 shows the result of a cation exchange column chromatography experiment carried out on a dialysed cheese whey salt-cut.

In the context of the present invention, the effect of aging may be any effect of aging. Thus the effect may be sagging of the skin, wrinkling of the skin or slow regeneration of damaged areas of skin. However, the effect is most preferably wrinkling of the skin. The periodontal disease is a disease of the gums. In the context of the present invention, this may be a gum disease arising for any reason, including infection of the teeth or gums as well as lack of cleaning (brushing or flossing) of the teeth or gums.

The polypeptide and polypeptide fragments used in the present invention may have either an alleviating effect, or a preventative effect, or both. Thus, they may have a prophylactic effect and/or may reduce the effects of gum disease or of aging, or provide protection against the onset of gum disease or may increase the youthful appearance of the skin.

Whilst the whole α-S2 casein precursor shows no significant efficacy against the effects of aging or gum disease, fragments of such proteins, such as polypeptides derived from the C-terminal end of α-S2 caseins, do have these effects. For example, the efficacy against gum disease and effects of aging is present in peptides which are derived from the C-terminal end of α-S2 casein precursors and have 3 or more amino acids, but do not comprise the N-terminal amino acid of the full α-S2 casein molecule. Thus, the casein-derived peptides and fragments used in the present invention generally comprise 3 or more amino acids and do not comprise the N-terminus of the full casein protein. In the context of the present invention, the peptide not comprising the N-terminal amino acid means that the peptide does not comprise the N-terminal end (N-terminus) of the protein itself. In some embodiments this can mean that the peptide does not comprise a number of amino acids up to and including the N-terminus. Preferably the peptides do comprise the C-terminus of the full protein.

Thus, the number of amino acids in the peptide or fragment used the present invention is not especially limited, provided that it has 3 or more amino acids, but does not comprise the N-terminal end of the full casein. However, it is preferred that the number of amino acids in the peptide is from 3-50, 4-50, 5-50, 6-50, or 7-50. Advantageously, the number of amino acids may be from 8-50 and more preferably from 9-50 or 10-50. It is particularly preferred that the upper limit on the amino acids in all these cases is 35 and most preferably 31. The most preferred number of amino acids is from 9-31.

Thus, the peptide may preferably comprise the last 3-50, 3-35 or 3-31 amino acids of the C-terminal end of the α-S2 casein precursor (including the C-terminus) and may even be as short as the last 3-10, 3-9, 3-8 or 3-7 or even just the last 3 amino acids of the C-terminal end of the α-S2 casein.

The bovine α-S2 casein precursor used in the present invention has the following amino acid sequence (SEQ ID NO:1):

```
[CAS2_BOVIN] ALPHA-S2 CASEIN PRECURSOR
SEQUENCE:
MKFFIFTCLL AVALAKNTME HVSSSEESII SQETYKQEKN

MAINPSKENL CSTFCKEVVR NANEEFYSIG SSSEESAEVA

TEEVKITVDD KHYQKALNEI NQFYQKFPQY LQYLYQGPIV

LNPWDQVKRN AVPITPTLNR EQLSTSEENS KKTVDMESTE

VFTKKTKLTE EEKNRLNFLK KISQRYQKFA LPQYLKTVYQ

HQKAMKPWIQ PKTKVIPYVR YL
```

In three letter codes this translates to:

```
Met Lys Phe Phe Ile Phe Thr Cys Leu Leu Ala Val

Ala Leu Ala Lys Asn Thr Met Glu His Val Ser Ser

Ser Glu Ser Ile Ile Ser Gln Glu Thr Tyr Lys

Gln Glu Lys Asn Met Ala Ile Asn Pro Ser Lys Glu

Asn Leu Cys Ser Thr Phe Cys Lys Glu Val Val Arg

Asn Ala Asn Glu Glu Glu Tyr Ser Ile Gly Ser Ser

Ser Glu Glu Ser Ala Glu Val Ala Thr Glu Glu Val

Lys Ile Thr Val Asp Asp Lys His Tyr Gln Lys Ala

Leu Asn Glu Ile Asn Gln Phe Tyr Gln Lys Phe Pro

Gln Tyr Leu Gln Tyr Leu Tyr Gln Gly Pro Ile Val

Leu Asn Pro Trp Asp Gln Val Lys Arg Asn Ala Val

Pro Ile Thr Pro Thr Leu Asn Arg Glu Gln Leu Ser

Thr Ser Glu Glu Asn Ser Lys Lys Thr Val Asp Met

Glu Ser Thr Glu Val Phe Thr Lys Lys Thr Lys Leu

Thr Glu Glu Glu Lys Asn Arg Leu Asn Phe Leu Lys

Lys Ile Ser Gln Arg Tyr Gln Lys Phe Ala Leu Pro

Gln Tyr Leu Lys Thr Val Tyr Gln His Gln Lys Ala

Met Lys Pro Trp Ile Gln Pro Lys Thr Lys Val Ile

Pro Tyr Val Arg Tyr Leu
```

It is preferred in the present invention that the peptide comprises an amino acid sequence selected from the following sequences (SEQ ID NOS:2-9, respectively):

```
LysValIleProTyrValArgTyrLeu;

ThrLysValIleProTyrValArgTyrLeu;

LysThrLysValIleProTyrValArgTyrLeu;
```

-continued

ProLysThrLysValIleProTyrValArgTyrLeu;

GlnProLysThrLysValIleProTyrValArgTyrLeu;

AlaMetLysProTrpIleGlnProLysThrLysValIleProTyrVal
ArgTyrLeu;

ThrValTyrGlnHisGlnLysAlaMetLysProTrpIleGlnProLys
ThrLysValIleProTyrValArgTyrLeu;
and ProGlnTyrLeuLysThrValTyrGlnHisGlnLysAlaMetLysPro
TrpIleGlnProLysThrLysValIleProTyrValArgTyrLeu.

These sequences all comprise the last 9 amino acids of the C-terminal end of the bovine α-S2 casein precursor. The present inventors have found that peptide sequences incorporating this C-terminal sequence, LysValIleProTyrValArgTyr-Leu (SEQ ID NO:2), show particularly marked anti-aging activity. Thus in a particularly preferred aspect of the present invention the polypeptide comprises a bovine α-S2 casein fragment comprising the sequence LysValIleProTyrValArg-TyrLeu (SEQ ID NO:2). Other particularly preferred sequences referred to above include the last 10, 11, 12 and 13 amino acids of the C-terminal end of the bovine α-S2 casein precursor. These amino acids are also the same as the last 7 amino acids of the goat and sheep α-S2 casein precursors, confirming the degree of similarity between these proteins, particularly at their C-termini It is also preferred in the present invention that the peptide comprises an amino acid sequence from the C-terminal end of the bovine α-S2 casein precursor, but without the last four C-terminal amino acids (i.e. without ValArgTyrLeu (SEQ ID NO:24)). Thus, the following sequences (SEQ ID NOS:16-23, respectively) are also preferred:

LysValIleProTyr;

ThrLysValIleProTyr;

LysThrLysValIleProTyr;

ProLysThrLysValIleProTyr;

GlnProLysThrLysValIleProTyr;

AlaMetLysProTrpIleGlnProLysThrLysValIleProTyr;

ThrValTyrGlnHisGlnLysAlaMetLysProTrpIleGlnProLys
ThrLysValIleProTyr;
and

ProGlnTyrLeuLysThrValTyrGlnHisGlnLysAlaMetLysPro
TrpIleGlnProLysThrLysValIleProTyr.

As highlighted above, there is a high degree of homology between the C-terminal end sequence of α-S2 casein precursors of bovine, goat, sheep, rabbit and pig origin. It is apparent from the sequences of these caseins that the C-terminal sequence can vary from species to species, but that there are important similarities. Accordingly, whilst bovine α-S2 casein precursor fragments are preferred for use in the present invention, goat, sheep, rabbit and pig α-S2 casein fragments, or similar fragments from other species, may also be employed if desired.

The sequences for α-S2 casein precursors of goat, sheep, rabbit and pig origin are set out below and assigned SEQ ID NOS:10-15, respectively.

In three letter codes, these sequences (SEQ ID NOS:10-15 respectively) translate to the following.

```
[CAS2 CAPH1] α-S2 casein precursor (α-S2-CN)
SEQUENCE:
Met    Lys    Phe    Ile    Phe    Phe    Thr    Cys    Leu    Leu
Ala    Val    Ala    Leu    Ala    Lys    His    Lys    Met    Glu
His    Val    Ser    Ser    Ser    Gly    Gly    Pro    Ile    Asn
Ile    Phe    Gln    Glu    Ile    Tyr    Lys    Gln    Glu    Lys
Asn    Met    Ala    Ile    His    Pro    Arg    Lys    Glu    Lys
Leu    Cys    Thr    Thr    Ser    Cys    Glu    Glu    Val    Val
Arg    Asn    Ala    Asn    Glu    Glu    Glu    Tyr    Ser    Ile
Arg    Ser    Ser    Ser    Glu    Glu    Ser    Ala    Glu    Val
Ala    Pro    Glu    Glu    Ile    Lys    Ile    Thr    Val    Asp
Asp    Lys    His    Tyr    Gln    Lys    Ala    Leu    Asn    Glu
Ile    Asn    Gln    Phe    Tyr    Gln    Lys    Phe    Pro    Gln
Tyr    Leu    Gln    Tyr    Pro    Tyr    Gln    Gly    Pro    Ile
Val    Leu    Asn    Pro    Trp    Asp    Gln    Val    Lys    Arg
Asn    Ala    Gly    Pro    Phe    Thr    Pro    Thr    Val    Asn
Arg    Glu    Gln    Leu    Ser    Thr    Ser    Glu    Glu    Asn
Ser    Lys    Lys    Thr    Ile    Asp    Met    Glu    Ser    Thr
Glu    Val    Phe    Thr    Lys    Lys    Thr    Lys    Leu    Thr
Glu    Glu    Glu    Lys    Asn    Arg    Leu    Asn    Phe    Leu
Lys    Lys    Ile    Ser    Gln    Tyr    Tyr    Gln    Lys    Phe
Ala    Trp    Pro    Gln    Tyr    Leu    Lys    Thr    Val    Asp
Gln    His    Gln    Lys    Ala    Met    Lys    Pro    Trp    Thr
Gln    Pro    Lys    Thr    Asn    Ala    Ile    Pro    Tyr    Val
Arg    Tyr    Leu >pir|S33881|S33881 α-S2 casein E - goat
SEQUENCE:
Met    Lys    Phe    Phe    Ile    Phe    Thr    Cys    Leu    Leu
Ala    Val    Ala    Leu    Ala    Lys    His    Lys    Met    Glu
His    Val    Ser    Ser    Ser    Glu    Glu    Pro    Ile    Asn
Ile    Phe    Gln    Glu    Ile    Tyr    Lys    Gln    Glu    Lys
Asn    Met    Ala    Ile    His    Pro    Arg    Lys    Glu    Lys
Leu    Cys    Thr    Thr    Ser    Cys    Glu    Glu    Val    Val
Arg    Asn    Ala    Asn    Glu    Glu    Glu    Tyr    Ser    Ile
Arg    Ser    Ser    Ser    Glu    Glu    Ser    Ala    Lys    Val
Ala    Pro    Glu    Glu    Ile    Lys    Ile    Thr    Val    Asp
```

```
[CAS2 CAPH1] α-S2 casein precursor (α-S2-CN)
SEQUENCE:
MKFFIFTCLL  AVALAKHKME  HVSSSEEPIN  IFQEIYKQEK  NMAIHPRKEK  LCTTSCEEVV
RNANEEEYSI  RSSSEESAEV  APEEIKITVD  DKHYQKALNE  INQFYQKFPQ  YLQYPYQGPI
VLNPWDQVKR  NAGPFTPTVN  REQLSTSEEN  SKKTIDMEST  EVFTKKTKLT  EEEKNRLNFL
KKISQYYQKF  AWPQYLKTVD  QHQKAMKPWT  QPKTNAIPYV  RYL         223

>pir|S33881|S33881 α-S2 casein E - goat
SEQUENCE:
MKFFIFTCLL  AVALAKHKME  HVSSSEEPIN  IFQEIYKQEK  NMAIHPRKEK  LCTTSCEEVV
RNANEEEYSI  RSSSEESAKV  APEEIKITVD  DKHYQKALNE  INQFYQKFPQ  YLQYPYQGPI
VLNPWDQVKR  NAGPFTPTVN  REQLSTSEEN  SKKTIDMEST  EVFTKKTKLT  EEEKNRLNFL
```

```
                                    -continued
KKISQYYQKF AWPQYLKTVD QHQKAMKPWT QPKTNAIPYV RYL          223

>gp|S74171|S74171_1 α-S2 casein C - capra hircus
SEQUENCE:
MKFFIFTCLL AVALAKHKME HVSSSEEPIN IFQEIYKQEK NMAIHPRKEK LCTTSCEEVV
RNANEEEYSI RSSSEESAEV APEEIKITVD DKHYQKALNE INQFYQKFPQ YLQYPYQGPI
VLNPWDQVKR NAGPFTPTVN REQLSTSEEN SKKTIDMEST EVFTKKTKLT EEEKNRLNFL
KIISQYYQKF AWPQYLKTVD QHQKAMKPWT QPKTNAIPYV RYL          223

>pir|S39776|S39776 α-S2 casein form b precursor - rabbit
>gp|X76909|OCPAS2BCS_1 pre-α-S2b casein (AA -15 to 167) Oryctolagus cuniculus
SEQUENCE:
MKFFTITCLL AVALAKEKIE QSSEETIAV SQEVSPNLEN ICSTACEEPI KNINEVEYVE
VPTEIKDQEF YQKVNLLQYL QALYQPTVM DPWTRAETKA IPFIRTMQYK QEKDATKHTS
QKTELTEEEK AFLKYLDEMK QYYQKFVFPQ YLKNAHHFQK TMNPWNHVKT IIYQVPTSL 179

[CAS2_SHEEP] α-S2 casein precursor - sheep
SEQUENCE:
MKFFIFTCLL AVALAKHKME HVSSSEEPIN ISQEIYKQEK NMAIHPRKEK LCTTSCEEVV
RNADEEEYSI RSSSEESAEV APEEVKITVD DKHYQKALNE INQFYQKFPQ YLQYLYQGPI
VLNPWDQVKR NAGPFTPTVN REQLSTSEEN SKKTIDMEST EVFTKKTKLT EEEKNRLNFL
KKISQYYQKF AWPQYLKTVD QHQKAMKPWT QPKTNAIPYV RYL          223

[CAS2_PIG] α-52 casein precursor - pig
SEQUENCE:
MKFFIFTCLL AVAFAKHEME HVSSSEESIN ISQEKYKQEK NVINHPSKED ICATSCEEAV
RNIKEVGYAS SSSSEESVDI PAENVKVTVE DKHYLKQLEK ISQFYQKFPQ YLQALYQAQI
VMNPWDQTKT SAYPFIPTVI QSGEELSTSE EPVSSSQEEN TKTVDESME EFTKKTELTE
EEKNRIKFLN KIKQYYQKFT WPQYIKTVHQ KQKAMKPWNH IKTNSYQIIP NLRYF 235
```

In three letter codes, these sequences (SEQ ID NOS:10-15, respectively) translate to the following:

```
[CAS2 CAPH1] α-S2 casein precursor (α-S2-CN)
SEQUENCE:
Met Lys Phe Ile Phe Phe Thr Cys Leu Leu
Ala Val Ala Leu Ala Lys His Lys Met Glu
His Val Ser Ser Ser Gly Gly Pro Ile Asn
Ile Phe Gln Glu Ile Tyr Lys Gln Glu Lys
Asn Met Ala Ile His Pro Arg Lys Glu Lys
Leu Cys Thr Thr Ser Cys Glu Glu Val Val
Arg Asn Ala Asn Glu Glu Glu Tyr Ser Ile
Arg Ser Ser Ser Glu Glu Ser Ala Glu Val
Ala Pro Glu Glu Ile Lys Ile Thr Val Asp
Asp Lys His Tyr Gln Lys Ala Leu Asn Glu
Ile Asn Gln Phe Tyr Gln Lys Phe Pro Gln
Tyr Leu Gln Tyr Pro Tyr Gln Gly Pro Ile
Val Leu Asn Pro Trp Asp Gln Val Lys Arg
Asn Ala Gly Pro Phe Thr Pro Thr Val Asn
Arg Glu Gln Leu Ser Thr Ser Glu Glu Asn
Ser Lys Lys Thr Ile Asp Met Glu Ser Thr
Glu Val Phe Thr Lys Lys Thr Lys Leu Thr
Glu Glu Glu Lys Asn Arg Leu Asn Phe Leu
Lys Lys Ile Ser Gln Tyr Tyr Gln Lys Phe
Ala Trp Pro Gln Tyr Leu Lys Thr Val Asp
Gln His Gln Lys Ala Met Lys Pro Trp Thr
Gln Pro Lys Thr Asn Ala Ile Pro Tyr Val
Arg Tyr Leu >pir|S33881|S33881 α-S2 casein E - goat
SEQUENCE:
Met Lys Phe Phe Ile Phe Thr Cys Leu Leu
Ala Val Ala Leu Ala Lys His Lys Met Glu
His Val Ser Ser Ser Glu Glu Pro Ile Asn
Ile Phe Gln Glu Ile Tyr Lys Gln Glu Lys
Asn Met Ala Ile His Pro Arg Lys Glu Lys
Leu Cys Thr Thr Ser Cys SLu Glu Val Val
Arg Asn Ala Asn Glu Glu Glu Tyr Ser Ile
Arg Ser Ser Ser Glu Glu Ser Ala Lys Val
Ala Pro Glu Glu Ile Lys Ile Thr Val Asp
Asp Lys His Tyr Gln Lys Ala Leu Asn Glu
Ile Asn Gln Phe Tyr Gln Lys Phe Pro Gln
Tyr Leu Gln Tyr Pro Tyr Gln Gly Pro Ile
Val Leu Asn Pro Trp Asp Gln Val Lys Arg
Asn Ala Gly Pro Phe Thr Pro Thr Val Asn
Arg Glu Gln Leu Ser Thr Ser Glu Glu Asn
Ser Lys Lys Thr Ile Asp Met Glu Ser Thr
                                    -continued
GLu Val Phe Thr Lys Lys Thr Lys Leu Thr
Glu Glu Glu Lys Asn Arg Leu Asn Phe Leu
Lys Lys Ile Ser Gln Tyr Tyr Gln Lys Phe
Ala Trp Pro Gln Tyr Leu Lys Thr Val Asp
Gln His Gln Lys Ala Met Lys Pro Trp Thr
Gln Pro Lys Thr Asn Ala Ile Pro Tyr Val
Arg Tyr Leu >gp |S7417|S74171_1 α-S2 casein C - capra hircus
SEQUENCE:
Met Lys Phe Ile Phe Thr Cys Leu Leu
Ala Val Ala Leu Ala Lys His Lys Met Glu
His Val Ser Ser Ser Glu Glu Pro Ile Asn
Ile Phe Gln Glu Ile Tyr Lys Gln Glu Lys
Asn Met Ala Ile His Pro Arg Lys Glu Lys
Leu Cys Thr Thr Ser Cys Glu Glu Val Val
Arg Asn Ala Asn Glu Glu Glu Tyr Ser Ile
Arg Ser Ser Ser Glu Glu Ser Ala Glu Val
Ala Pro Glu Glu Ile Lys Ile Thr Val Asp
Asp Lys His Tyr Gln Lys ALa Leu Asn Glu
Ile Asn Gln Phe Tyr Gln Lys Phe Pro Gln
Tyr Leu Gln Tyr Pro Tyr Gln Gly Pro Ile
Val Leu Asn Pro Trp Asp Gln Val Lys Arg
Asn Ala Gly Pro Phr Thr Pro Thr Val Asn
Arg Glu Gln Leu Ser Thr Ser Glu Glu Asn
Ser Lys Lys Thr Ile Asp Met Glu Ser Thr
Glu Val Phe Thr Lys Lys Thr Lys Leu Thr
Glu Glu Glu Lys Asn Arg Leu Asn Phe Leu
Lys Ile Ile Ser Gln Tyr Tyr Gln Lys Phe
Ala Trp Pro Gln Tyr Ley Lys Thr Val Asp
Gln His Gln Lys ALa Met Lys Pro Trp Thr
Gln Pro Lys Thr Asn Ala Ile Pro Tyr Val
Arg Tyr Leu >pir|S39776|S39776 α-S2 casein form b precursor -
rabbit
>gp|X76909|OCPAS2BCS_1 pre-α-S2b casein
(AA -to 167) Oryctolagus cuniculus
SEQUENCE:
Met Lys Phe Phe Ile Phe Thr Cys Leu Leu
Ala Val Ala Leu Ala Lys Pro Lys Ile Glu
Gln Ser Ser Ser Glu Glu Thr Ile Ala Val
Ser Gln Glu Val Ser Pro Asn Leu Glu Asn
Ile Cys Ser Thr Ala Cys Glu Glu Pro Ile
Lys Asn Ile Asn Glu Val Glu Tyr Val Glu
Val Pro Thr Glu Ile Lys Asp Gln Glu Phe
```

-continued
```
Tyr Gln Lys Val Asn Leu Leu Gln Tyr Leu
Gln Ala Leu Tyr Gln Tyr Pro Thr Val Met
Asp Pro Trp Thr Arg Ala Glu Thr Lys Ala
Ile Pro Phe Ile Arg Thr Met Gln Tyr Lys
Gln Glu Lys Asp Ala Thr Lys His Thr Ser
Gln Lys Thr Glu Leu Thr Glu Glu Glu Lys
Ala Phe Leu Lys Tyr Leu Asp Glu Met Lys
Gln Tyr Tyr Gln Lys Phe Val Phe Pro Gln
Tyr Leu Lys Asn Ala His His Phe Gln Lys
Thr Met Asn Pro Trp Asn His Val Lys Thr
Ile Ile Tyr Gln Ser Val Pro Thr Leu

[CAS2_SHEEP] α-S2 casein precursor - sheep
SEQUENCE:
Met Lys Phe Phe Ile Phe Thr Cys Leu Leu
Ala Val Ala Leu Ala Lys His Lys Met Glu
His Val Ser Ser Ser Glu Glu Pro Ile Asn
Ile Ser Gln Glu Ile Tyr Lys Gln Glu Lys
Asn Met Thr Thr Ser Cys Glu Glu Val Val
Arg Asn Ala Asp Glu Glu Glu Tyr Ser Ile
Arg Ser Ser Ser Glu Glu Ser Ala Glu Val
Ala Pro Glu Glu Val Lys Ile Thr Val Asp
Asp Lys His Tyr Gln Lys Ala Leu Asn Glu
Ile Asn Gln Phe Tyr Gln Lys Phe Pro Gln
Tyr Leu Gln Tyr Leu Tyr Gln Gly Pro Ile
Val Leu Asn Pro Trp Asp Gln Val Lys Arg
Asn Ala Gly Pro Phe Thr Pro Thr Val Asn
Arg Glu Gln Leu Ser Thr Ser Glu Glu Asn
Ser Lys Lys Thr Ile Asp Met Glu Ser Thr
Glu Val Phe Thr Lys Lys Thr Lys Leu Thr
Glu Glu Glu Lys Asn Arg Leu Asn Phe Leu
Lys Lys Ile Ser Gln Tyr Tyr Gln Lys Phe
Ala Trp Pro Gln Tyr Leu Lys Thr Val Asp
Gln His Gln Lys ALa Met Lys Pro Trp Thr
Gln Pro Lys Thr Asn Ala Ile Pro Tyr Val
Arg Tyr Leu

[CAS2_PIG] α-S2 casein precursor - pig
SEQUENCE:
Met Lys Phe Phe Ile Phe Thr Cys Leu Leu
Ala Val Ala Phe Ala Lys His Glu Met Glu
His Val Ser Ser Ser Glu Glu Ser Ile Asp
Ile Ser Gln Glu Lys Tyr Lys Gln Glu Lys
Asn Val Ile Asn His Pro Ser Lys Glu Asp
Ile Cys Ala Thr Ser Cys Glu Glu Ala Val
Arg Asn Ile Lys Glu Val Glu Tyr Ala Ser
Ser Ser Ser Ser Glu GLu Ser Val Asp Ile
Pro Ala Glu Asn Val Lys Val Thr Val Glu
Asp Lys His Tyr Leu Lys Gln Leu Glu Lys
Ile Ser Gln Phe Tyr Gln Lys Phe Pro Gln
Tyr Leu Gln Ala Leu Try Gln Ala Gln Ile
Val Met Asn Pro Trp Asp Gln Thr Lys Thr
Ser ALa Tyr Pro Phe Ile Pro Thr Val Ile
Gln Ser Gly Glu Glu Leu Ser Thr Ser Glu
Glu Pro Val Ser Ser Ser Gln Glu Glu Asn
Thr Lys Thr Val Asp Met Glu Ser Met Glu
Glu Phe Thr Lys Lys Thr Glu Leu Thr Glu
Glu Glu Lys Asn Arg Ile Lys Phe Leu Asn
Lys Ile Lys Gln Tyr Tyr Gln Lys Phe Thr
Trp Pro Gln Tyr Ile Lys Thr Val His Gln
Lys Gln Lys Ala Met Lys Pro Trp Asn His
Ile Lys Thr Asn Ser Tyr Gln Ile Ile Pro
Asn Leu Arg Tyr Phe
```

Furthermore, due to the similar nature of some amino acids it is possible to interchange some amino acids without affecting the functioning of the sequence. Accordingly leucine, isoleucine and valine may be interchanged. In addition tyrosine and phenylalanine may also be interchanged, as may arginine and lysine.

The invention will now be discussed in more detail. The invention preferably relates to α-S2 casein precursor fragments, and more preferably to the peptides referred to in WO 97/16460, for use as a cosmetic product, preferably in a cream or lotion, for reducing an aging effect in skin, such as wrinkles. The invention is preferably applicable to human skin, but may if desired be applied to other skin such as mammalian skin generally.

The invention also relates to the α-S2 casein precursor fragments mentioned above for use as a prophylactic agent or treatment agent for periodontal disease. This preferably relates to such diseases in humans, but may also apply to such diseases in mammalian gums generally if desired. The agent may be in any suitable form, such as a topical agent (e.g. a toothpaste for cleaning the teeth and/or gums) or a chewing gum.

The peptides may be used as a pure product, or may conveniently be supplied as an enriched natural preparation from milk by following the protocols described in WO 97/16460 as far as (and including) the hydrophobic interaction chromatography step. Alternatively, cheese whey may be used in place of the acid (milk) whey.

The peptides may be used alone, or in combination with acceptable (in some cases pharmaceutically acceptable) additives and/or excipients useful for formulating topical compositions, toothpastes, or chewing gums. Additives for topical agents may include, for example, moisturising agents and/or other agents beneficial to the skin, such as all or any of vitamins A, C, D and E, that are used to beneficial effect to prevent/reverse the aging of skin.

Without being bound by theory, it is believed that the basis of the invention is that the peptides stimulate the production of fibrillin in fibroblasts, especially dermal fibroblasts. This is believed to ameliorate the fibrillin-rich microfibrillar network proximal to the dermal-epidermal junction of aged skin. Thus the peptides are capable of repairing the fibrillin deficit in aged (especially photoaged) skin.

The peptides used in the present invention appear to fulfill the equivalent role in bovine milk that EGF does in other species. The present inventors have surprisingly discovered that these peptides are effective as anti-periodontal disease agents and anti-aging agents and are more effective than known products. A further advantage of the peptides used in the present invention is that whilst they have an efficacy similar to, or are superior to, EGF they are regarded as being 'natural products' (being milk-derived) and because they have essentially no full protein content, they are not allergenic.

In the present invention the peptide, or derivative of the peptide, can be used in the manufacture of a medicament effective in alleviating or preventing an effect of aging in skin, wherein the peptide has an α-S2 casein fragment activity. Thus the peptide may be an α-S2 casein precursor fragment, as described in detail above, or can be a related molecule having a similar activity, such as a homologue. The peptides are particularly effective against photoaging. In the present context, photoaging of skin means the effects of cumulative exposure to ultra-violet radiation and/or sunlight, or alternatively the combination of chronological ageing and the effects of cumulative exposure to ultra-violet radiation and/or sunlight. Typically, it is manifested clinically by coarse and fine wrinkling, dyspigmentation, sallowness and the formation of benign and malignant neoplasms. The mechanisms of wrinkle formation are not fully understood, but without being bound by theory, it is thought that the glycoprotein fibrillin may be important. Fibrillin is a major constituent of the elastin network in the papillary dermis and plays an important role in maintaining the integrity of the basement membrane zone. The present invention relates to methods of repairing the basement membrane zone, by stimulating the production of fibrillin.

Also in the present invention, the peptide, or derivative of the peptide, can be used in the manufacture of a medicament effective in alleviating or preventing periodontal disease, wherein the peptide has an α-S2 casein fragment activity.

Thus, as in the related aspect, the peptide may be an α-S2 casein precursor fragment, as described in detail above, or can be a related molecule having a similar activity, such as a homologue.

Preferably the peptide used in the present invention is capable of stimulating the growth of fibroblasts. It is also preferred that the peptide is capable of stimulating fibroblasts to produce collagen. It is further preferred that the peptide is capable of stimulating growth in keratinocytes.

In a further aspect, the present invention provides a cosmetic method, or a medical method, for alleviating or preventing an effect of aging in skin by stimulating the production of fibrillin in fibroblasts, which method comprises treating a subject with a peptide, wherein the peptide comprises an amino acid sequence present in an α-S2 casein precursor, said sequence comprising 3 or more amino acids, and not comprising at its N-terminus the N-terminal amino acid of the full α-S2 casein precursor. The peptide is preferably a specific peptide as discussed in detail above, but alternatively may be an α-S2 casein precursor fragment, or a related molecule having a similar activity, such as a homologue.

In a still further aspect, the present invention provides a topical composition for stimulating the production of fibrillin by fibroblasts, comprising a peptide, or a derivative of a peptide, wherein the peptide comprises an amino acid sequence present in an α-S2 casein precursor, said sequence comprising 3 or more amino acids, and not comprising at its N-terminus the N-terminal amino acid of the full α-S2 casein precursor. The peptide is preferably a specific peptide as discussed in detail above, but alternatively may be an α-S2 casein precursor fragment, or a related molecule having a similar activity, such as a homologue.

In a related aspect, the invention provides a pharmaceutical composition for alleviating or preventing periodontal disease by stimulating the production of fibrillin by fibroblasts, comprising a peptide, or a derivative of a peptide, wherein the peptide comprises an amino acid sequence present in an α-S2 casein precursor, said sequence comprising 3 or more amino acids, and not comprising at its N-terminus the N-terminal amino acid of the full α-S2 casein precursor. Again, the peptide is preferably a specific peptide as discussed in detail above, but alternatively may be an α-S2 casein precursor fragment, or a related molecule having a similar activity, such as a homologue.

The invention will be further described by way of example only with reference to the following specific embodiments.

6. EXAMPLES

Example 1

Preparation of Standardised Natural Product from Cheese Whey

This procedure covers the methods for the collection, preparation and storage of Standardised Natural Product (SNP) from cheese whey. Typically, this procedure is used for small-scale preparation of SNP, such as for research and development purposes. However, the procedure can be scaled up as desired for commercial production according to known techniques.

Collection and Storage of Cheese Whey

Approximately 40 l of fresh clarified cheese whey was obtained from DewLay cheese manufacturing plant (Garstang, Lancashire). The whey was collected in clean containers and immediately transported to Pepsyn Central Manufacturing Facility (Liverpool).

Whey was either refrigerated for processing the following day or the whey was frozen at −20° C. in shallow 2 l containers until required.

Thawing of Cheese Whey

Frozen whey was thawed by placing a 2 l block of whey in a plastic bag and immersing it in hot running water. Thawing was completed in less than 10 mins and the temperature of the melting whey was maintained below 10° C.

Salting Out

The pH of the whey was adjusted to 3.0 using concentrated HCl. To each liter of whey, 220 g of $(NH_4)_2SO_4$ (BDH, AnalaR grade) was slowly added over a period of 30 mins whilst stirring. It was left to equilibrate for a further 1 hr 30 mins without stirring, and then centrifuged at 9000 rpm for 40 mins using a SorvallRC-5B centrifuge and associated GS-3 rotor (DuPont Instruments), which were pre-equilibrated to an operating temperature of between 4 and 10° C. To each litre of supernatant recovered, 130 g of $(NH_4)_2SO_4$ was added, and left to equilibrate and centrifuged as described above. The supernatant was discarded and the pellet was redissolved in distilled water (400 ml for each liter of whey started with). This was dialysed with visking tubing MWCO 12,000 to 14,000 daltons (Medicell Int. Ltd, UK) against running tap water overnight and then with 20 mM sodium phosphate buffer at pH 6.0 for 7 hr with one change of buffer. The dialysed salt-cut was collected and either refrigerated for processing the following day or frozen (−20° C.) until required.

Cation Exchange Chromatography

Dialysed cheese whey salt-cut was run on cation-exchange chromatography, at 4° C. with a mobile phase of 20 mM sodium phosphate buffer, pH 6.0. Protein was eluted using a linear salt gradient of 100 to 700 mM NaCl provided by a gradient mixer (Pharmacia gradient mixer GM-1). The progress of the run was monitored at 280 nm using a UV monitor (Uvicord S II, Pharmacia).

A cation exchange column (Pharmacia XK50series, 50 mm i.d.) was prepared with CM52 carboxymethyl (Whatman) to a packed bed height of 15 cm. This was equilibrated with 500 ml of buffer solution. Dialysed cheese whey salt cut (400 ml) was loaded on the column at a flow rate of 2.5 ml/min and then washed overnight with 500 ml of 50 mM NaCl in buffer at a flow rate of about 0.5 ml/min. A 500 ml linear gradient of 100 to 700 mM NaCl in buffer was applied at a 2.0 ml/min and fractions were collected every 25 ml and numbered sequentially. The column was then washed with 300 ml of 2M NaCl in buffer. Collected fractions were tested for growth promoting activity. This was typically observed in fraction numbers 11 and 12 that contained lactoferrin, and also in the fractions just before and after these (see FIG. 1). Because lactoferrin gave a brown appearance to the fractions then this was used as a visual marker for activity. The mean estimated concentration of NaCl in each of the collected fractions is given in Table 1. All fractions were frozen until required for the next chromatographic step.

TABLE 1

Concentration of NaCl in each fraction from CM52 run.

| Fraction | Estimated NaCl (mM) |
|---|---|
| 5 | 115 |
| 6 | 145 |
| 7 | 175 |
| 8 | 205 |
| 9 | 235 |
| 10 | 265 |
| 11 | 295 |

TABLE 1-continued

Concentration of NaCl in each fraction from CM52 run.

| Fraction | Estimated NaCl (mM) |
|---|---|
| 12 | 325 |
| 13 | 355 |
| 14 | 385 |
| 15 | 415 |
| 16 | 445 |
| 17 | 475 |
| 18 | 505 |
| 19 | 535 |
| 20 | 565 |
| 21 | 595 |
| 22 | 625 |
| 23 | 655 |
| 24 | 685 |

N. B. the column inlet and outlet there was approximately 100 ml excluded volume. Therefore fraction 1 to 4 contained 50 mM NaCl from the wash buffer.

Hydrophobic Interaction Chromatography

Active fractions from cation exchange chromatography were run on hydrophobic interaction chromatography (HIC). This was performed at room temperature with a mobile phase of 20 mM sodium phosphate buffer at pH 6.5. Protein was eluted using a linear salt gradient of 4 to 0 M NaCl provided by a gradient mixer (Pharmacia gradient mixer GM-1). of the run was monitored at 280 nm using a UV monitor (Uvicord S II, Pharmacia).

A HIC column (Pharmacia C series, 26 mm i.d.) was prepared with Butyl Sepharose 4 Fase Flow (Pharmacia) to give a packed bed height of 15 cm. The column was equilibrated overnight with 250 ml of 4 M NaCl in buffer at a flow rate of 0.25 ml/min.

The active fractions from several cation exchange chromatography runs were pooled together to give between 100 and 200 ml of sample. The mean concentration of NaCl in this sample was calculated from the estimated concentrations of NaCl in the constituent fractions (Table 1). Solid NaCl was then slowly added to the sample to make it 3.7 M, and the pH was adjusted to 6.5. Sample was loaded on the column at 2.0 ml/min. A 500 ml eluting gradient of 4 M to 0 M NaCl was applied and fractions were collected every 25 ml and numbered sequentially. The column was then washed with 250 ml of buffer followed by 250 ml of water.

Figure 2:
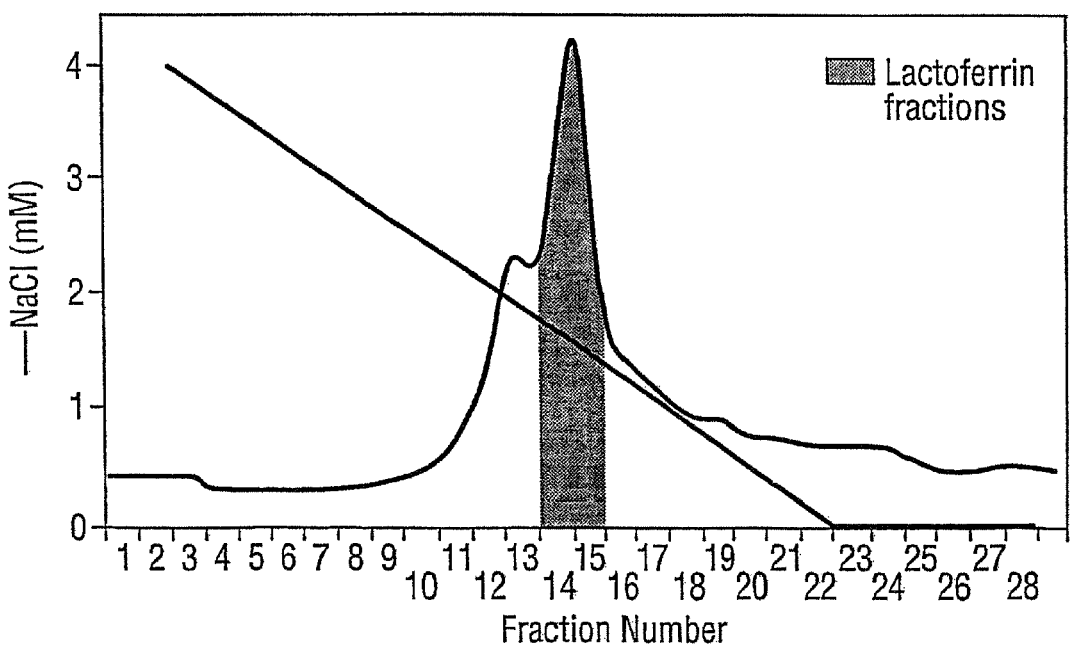
FIG. 2 shows the results of a hydrophobic interaction column chromatography experiment performed on active fractions from cation exchange chromatography.

Collected fractions were tested for growth promoting activity. This was typically observed in fraction numbers 10 to 13, which were the fractions that eluted just before the brown lactoferrin fractions (see FIG. 2). Active fractions were pooled, extensively dialysed against distilled water and freeze-dried.

Example 2

Demonstration that SNP Increases Fibrillin Synthesis in vivo in Humans

This Example shows that the peptides employed in the present invention stimulate the replacement of fibrillin in vivo, aiding in the repair of skin that has been photoaged. The peptides thus have clinical efficacy.

The study involves a topical application of casein peptides (36 μg SNP/ml of water; SNP was produced in accordance with Example 1) to determine the change in the expression of fibrillin and pro-collagen I in photoaged skin. Occlusion-only controls were also studied.

Patch-Test Control

Ten healthy, but photoaged, volunteers were recruited (male: 7; female: 3; age range 37-77 years). Test substances were applied separately under standard 6 mm diameter Finn chambers to the extensor aspect of the forearm; these were casein peptides (36 μg SNP/ml water), and occluded baseline control. After treatment for 4 days the Finn chambers were removed, and a 3 mm punch biopsy was be obtained under 1 vol.% lignocaine anaesthesia from each test site. Each biopsy was snap frozen in liquid nitrogen and processed histological assessment. Biopsy sites were sutured with 1×4/o ethilon and subjects instructed to return in 7 days for suture removal.

Fibrillin Examination by Immunohistochemistry

Frozen sections were prepared at a thickness of 10 μm (OTF cryostat, Bright Instruments Ltd.). Three sections per area per patient were treated as follows to identify the fibrillin-rich microfibrillar network by light microscopy:

Sections were fixed with 4 vol.% paraformaldehyde in phosphate-buffered saline (10 mins). Following hydration in tris-buffered saline (TBS; 100 mM Tris, 150 mM NaCl), sections were solubilised by addition of 0.5 vol.% Triton-X 100® (10 mins). Following washing, endogenous peroxidase activity was abolished by incubation with an excess of hydrogen peroxide in methanol (30 mins). All sections were then blocked with 1 vol.% normal horse serum+1 vol.% bovine serum albumen, prior to application of primary antibody (mouse anti-human fibrillin-1, clone 11C1.3; NeoMarkers, Calif., USA) at a dilution of 1:100. Negative controls were concurrently incubated with either block alone or control mouse serum at a dilution of 1:100. Following incubation, sections were stringently washed with TBS prior to application of the horse anti-mouse IgG biotinylated secondary antibody. This was further conjugated to the enzyme horseradish peroxidase using a commercially available kit following the manufacturers instructions (ABC Elite System, Vector Laboratory, Peterborough UK). Antibody was localised using 3',3'-diaminobenzadine as chromogen (10 mins incubation). Washing in TBS quenched this reaction. Sections were counterstained using nuclear fast red and finally dehydrated through serial alcohols, cleared and permanently mounted.

Sections were randomised, blinded and examined on a Nikon OPTIPHOT microscope (Tokyo, Japan). The degree of immunostaining was assessed on a 5 point semi-quantitative scale where 0=no staining and 4=maximal staining. Four sections (including control) were examined per subject per site. The degree of immunostaining was scored for three high power fields per section, and the average score calculated for each site/test area.

Differences in the distribution of fibrillin protein between the test sites, and after application of test substances for varying periods of time, were assessed for significance using the analysis of variance test (ANOVA; SPSS+ v10.0, SPSS Inc., IL USA).

The majority of volunteers tolerated the casein patch test protocol well; of the 10, only one individual complained of tenderness at the site of the casein application. The casein peptide patch produced deposition of fibrillin-1 proximal to the dermal/epidermal junction (base membrane zone) in 7/10 individuals (the volunteer who had complained of tenderness was amongst the 3 "non-responders" in this trial).

A known agent for stimulating fibrillin production is all-trans retinoic acid (RA). However, a drawback of this agent is that it produces marked erythema at the site of application. None of the above subjects produced erythema following application of casein, showing the advantage of this agent over all-trans retinoic acid.

Figure 3:
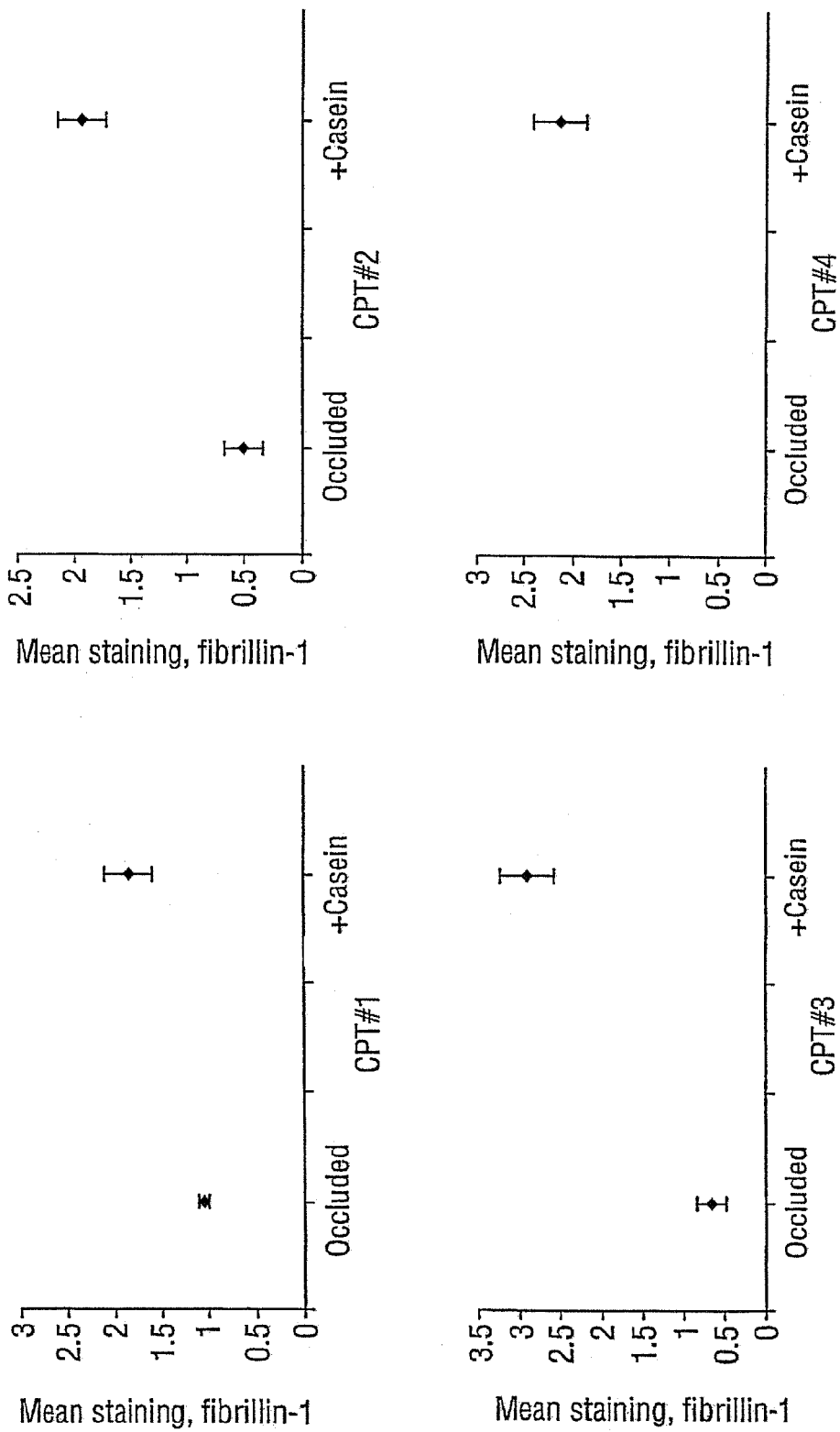
FIG. 3 shows fibrillin production in ten human volunteers treated with peptides of the present invention, compared with occluded controls.

Individual performance data is shown in FIG. 3. The mean data per volunteer was then pooled and is shown graphically in FIG. 4; all data is presented as means+ SEM. In brief, it was found that casein had a very positive effect on the fibrillin-rich microfibrillar network of the papillary dermis over that of baseline (occluded: 0.93=0.21; casein: 1.86=0.39; p=0.023).

From this Example it can be seen that topical application of casein peptides (under occlusion) ameliorates the fibrillin-rich microfibrillar network proximal to the dermal-epidermal junction of photoaged skin. These results show that casein peptides used in the present invention can repair the fibrillin deficit in photoaged skin and/or aged skin, and have clear clinical utility.

Example 3

Demonstration that SNP Increases Collagen Synthesis in Fibroblasts

Rama 27 rat mammary cells were grown to confluence, and their rate of synthesis of collagen was measured using the method of M. J. Warburton, S. A. Ferns, and P. S. Rudland, *Experimental Cell Research*, 137, 373-380 (1982). The rates of collagen synthesis as estimated by the incorporation of [3H]proline into hydroxyproline are set out in Table 2 below:

TABLE 2

Rates of collagen synthesis

| Concentration of SNP (mg/ml) | Cellular HO-proline (cpm) | Secreted HO-proline (cpm) |
|---|---|---|
| 0 | 53 | 54 |
| 0.2 | 271 | 233 |
| 0.4 | 232 | 327 |
| 0.6 | 321 | 663 |

Adding up to 0.6 mg/ml of SNP gives rise to an approximate 12-fold increase in the secretion of collagen—from 54 cpm to 663 cpm. This also gives rise to an approximate doubling in the ratio of synthesised collagen that is secreted to that which is retained in the cell—from 54:53 (1:1) to 663:321 (2:1).

Example 4

Demonstration of the Effect of SNP on the Growth of Keratinocytes

Human keratinocytes (HatKat) were grown in keratinocyte growth medium (TCS Cellworks Ltd.) until 20% confluence. Then, in the same medium, the keratinocytes were grown for three days with 0.5% foetal calf serum (FCS), at which point the cells were counted in a Coulter® counter. The cell numbers obtained are set out in Table 3 below.

TABLE 3

| | Cell numbers |
|---|---|
| Conditions of growth | Number of cells |
| Medium with 0.5% FCS | 23,777 |
| Medium with 0.5% FCS + 10 ng/ml EGF | 29,356 |
| Medium with 0.5% FCS + 0.6 mg/ml SNP | 68,719 |

This shows that the presence of SNP gives rise to an approximate 3-fold increase in the growth of keratinocytes—from 23,777 to 68,719. This compares with a relatively modest increase with the use of 10 ng/ml EGF.

These results clearly demonstrate the collagen producing activity and growth promoting activity of the peptides used in the present invention.

The invention claimed is:

1. A pharmaceutical composition comprising an excipient and a peptide selected from the group consisting of:

```
Lys Val Ile Pro Tyr [SEQ ID NO: 16];

Thr Lys Val Ile Pro Tyr [SEQ ID NO: 17];

Lys Thr Lys Val Ile Pro Tyr [SEQ ID NO: 18];

Pro Lys Thr Lys Val Ile Pro Tyr [SEQ ID NO: 19];

Gln Pro Lys Thr Lys Val Ile Pro Tyr
[SEQ ID NO: 20];

Ala Met Lys Pro Trp Ile Gln Pro Lys Thr Lys Val
Ile Pro Tyr [SEQ ID NO: 21];

Thr Val Tyr Gln His Gln Lys Ala Met Lys Pro Trp
Ile Gln Pro Lys Thr Lys Val Ile Pro Tyr [SEQ ID NO:
22];

Pro Gln Tyr Leu Lys Thr Val Tyr Gln His Gln Lys Ala
Met Lys Pro Trp Ile Gln Pro Lys Thr Lys Val Ile Pro
Tyr [SEQ ID NO: 23]; and
``` a peptide wherein one or more of the Leu, Ile or Val amino acid residues in SEQ ID NO:17 to 23 is substituted with a non-identical amino acid selected from the group consisting of Leu, Ile and Val, and/or
   wherein one or more of the Tyr amino acid residues is substituted with a Phe amino acid, and/or
   wherein one or more of the Lys amino acid residues is substituted with an Arg amino acid.

2. The pharmaceutical composition of claim 1, wherein the composition is formulated for topical administration.

3. The pharmaceutical composition of claim 1, wherein the composition is formulated for administration in a chewing gum.

4. The pharmaceutical composition of claim 1, wherein the composition is formulated for administration in a toothpaste.

5. A method for increasing fibrillin deposition in skin, comprising contacting skin with an amount of a composition effective to increase fibrillin deposition in skin, which composition comprises a peptide selected from the group consisting of:

```
Lys Val Ile Pro Tyr [SEQ ID NO: 16];

Thr Lys Val Ile Pro Tyr [SEQ ID NO: 17];

Lys Thr Lys Val Ile Pro Tyr [SEQ ID NO: 18];

Pro Lys Thr Lys Val Ile Pro Tyr [SEQ ID NO: 19];

Gln Pro Lys Thr Lys Val Ile Pro Tyr
[SEQ ID NO: 20];

Ala Met Lys Pro Trp Ile Gln Pro Lys Thr Lys Val
Ile Pro Tyr [SEQ ID NO: 21];

Thr Val Tyr Gln His Gln Lys Ala Met Lys Pro Trp
Ile Gln Pro Lys Thr Lys Val Ile Pro Tyr [SEQ ID NO:
22];

Pro Gln Tyr Leu Lys Thr Val Tyr Gln His Gln Lys Ala
Met Lys Pro Trp Ile Gln Pro Lys Thr Lys Val Ile Pro
Tyr [SEQ ID NO: 23]; and
``` a peptide wherein one or more of the Leu, Ile or Val amino acid residues in SEQ ID NO:16 to 23 is substituted with a non-identical amino acid selected from the group consisting of Leu, Ile and Val, and/or
   wherein one or more of the Tyr amino acid residues is substituted with a Phe amino acid, and/or
   wherein one or more of the Tyr amino acid residues is substituted with a Phe amino acid.

6. The method of claim 5, wherein the composition is formulated for topical administration.

7. The method of claim 5, wherein the composition is formulated for administration in a chewing gum.

8. The method of claim 5, wherein the composition is formulated for administration in a toothpaste.

9. The method of claim 5, wherein said composition is applied topically to the skin.

10. The method of claim 5, wherein the skin that is contacted is photoaged skin.

11. The method of claim 5, wherein the skin that is contacted is located in the gums.

12. A method for stimulating growth of fibroblasts, comprising contacting a fibroblast with an amount of a peptide effective to stimulate growth of fibroblasts, which peptide is selected from the group consisting of:

```
Lys Val Ile Pro Tyr [SEQ ID NO: 16];

Thr Lys Val Ile Pro Tyr [SEQ ID NO: 17];

Lys Thr Lys Val Ile Pro Tyr [SEQ ID NO: 18];

Pro Lys Thr Lys Val Ile Pro Tyr [SEQ ID NO: 19];

Gln Pro Lys Thr Lys Val Ile Pro Tyr
[SEQ ID NO: 20];

Ala Met Lys Pro Trp Ile Gln Pro Lys Thr Lys Val
Ile Pro Tyr [SEQ ID NO: 21];

Thr Val Tyr Gln His Gln Lys Ala Met Lys Pro Trp
Ile Gln Pro Lys Thr Lys Val Ile Pro Tyr [SEQ ID NO:
22];

Pro Gln Tyr Leu Lys Thr Val Tyr Gln His Gln Lys Ala
Met Lys Pro Trp Ile Gln Pro Lys Thr Lys Val Ile Pro
Tyr [SEQ ID NO: 23].
```

13. A method for stimulating growth of keratinocytes, comprising contacting a keratinocyte with an amount of a peptide effective to stimulate growth of keratinocytes, which peptide is selected from the group consisting of:

Lys Val Ile Pro Tyr [SEQ ID NO: 16];

Thr Lys Val Ile Pro Tyr [SEQ ID NO: 17];

Lys Thr Lys Val Ile Pro Tyr [SEQ ID NO: 18];

Pro Lys Thr Lys Val Ile Pro Tyr [SEQ ID NO: 19];

Gln Pro Lys Thr Lys Val Ile Pro Tyr [SEQ ID NO: 20];

Ala Met Lys Pro Trp Ile Gln Pro Lys Thr Lys Val Ile Pro Tyr [SEQ ID NO: 21];

Thr Val Tyr Gln His Gln Lys Ala Met Lys Pro Trp Ile Gln Pro Lys Thr Lys Val Ile Pro Tyr [SEQ ID NO: 22];

Pro Gln Tyr Leu Lys Thr Val Tyr Gln His Gln Lys Ala Met Lys Pro Trp Ile Gln Pro Lys Thr Lys Val Ile Pro Tyr [SEQ ID NO: 23].

* * * * *

SEQUENCE LISTING

```
<160> NUMBER OF SEQ ID NOS: 24

<210> SEQ ID NO 1
<211> LENGTH: 222
<212> TYPE: PRT
<213> ORGANISM: Bos taurus
<220> FEATURE:
<221> NAME/KEY: PROPEP
<222> LOCATION: (1)..(222)
<223> OTHER INFORMATION: Amino acid sequence of bovine alpha-S2 casein
      precursor.

<400> SEQUENCE: 1

Met Lys Phe Phe Ile Phe Thr Cys Leu Leu Ala Val Ala Leu Ala Lys
1               5                   10                  15

Asn Thr Met Glu His Val Ser Ser Ser Glu Glu Ser Ile Ile Ser Gln
            20                  25                  30

Glu Thr Tyr Lys Gln Glu Lys Asn Met Ala Ile Asn Pro Ser Lys Glu
        35                  40                  45

Asn Leu Cys Ser Thr Phe Cys Lys Glu Val Val Arg Asn Ala Asn Glu
    50                  55                  60

Glu Glu Tyr Ser Ile Gly Ser Ser Ser Glu Glu Ser Ala Glu Val Ala
65                  70                  75                  80
```

```
Thr Glu Glu Val Lys Ile Thr Val Asp Asp Lys His Tyr Gln Lys Ala
                85                  90                  95

Leu Asn Glu Ile Asn Gln Phe Tyr Gln Lys Phe Pro Gln Tyr Leu Gln
            100                 105                 110

Tyr Leu Tyr Gln Gly Pro Ile Val Leu Asn Pro Trp Asp Gln Val Lys
        115                 120                 125

Arg Asn Ala Val Pro Ile Thr Pro Thr Leu Asn Arg Glu Gln Leu Ser
    130                 135                 140

Thr Ser Glu Glu Asn Ser Lys Lys Thr Val Asp Met Glu Ser Thr Glu
145                 150                 155                 160

Val Phe Thr Lys Lys Thr Lys Leu Thr Glu Glu Lys Asn Arg Leu
                165                 170                 175

Asn Phe Leu Lys Lys Ile Ser Gln Arg Tyr Gln Lys Phe Ala Leu Pro
            180                 185                 190

Gln Tyr Leu Lys Thr Val Tyr Gln His Gln Lys Ala Met Lys Pro Trp
        195                 200                 205

Ile Gln Pro Lys Thr Lys Val Ile Pro Tyr Val Arg Tyr Leu
    210                 215                 220

<210> SEQ ID NO 2
<211> LENGTH: 9
<212> TYPE: PRT
<213> ORGANISM: Bos taurus
<220> FEATURE:
<221> NAME/KEY: PEPTIDE
<222> LOCATION: (1)..(9)
<223> OTHER INFORMATION: Amino acid sequence of peptide derived from
      bovine alpha-2 casein precursor.

<400> SEQUENCE: 2

Lys Val Ile Pro Tyr Val Arg Tyr Leu
1               5

<210> SEQ ID NO 3
<211> LENGTH: 10
<212> TYPE: PRT
<213> ORGANISM: Bos taurus
<220> FEATURE:
<221> NAME/KEY: PEPTIDE
<222> LOCATION: (1)..(10)
<223> OTHER INFORMATION: Amino acid sequence of peptide derived from
      bovine alpha-2 casein precursor.

<400> SEQUENCE: 3

Thr Lys Val Ile Pro Tyr Val Arg Tyr Leu
1               5                   10

<210> SEQ ID NO 4
<211> LENGTH: 11
<212> TYPE: PRT
<213> ORGANISM: Bos taurus
<220> FEATURE:
<221> NAME/KEY: PEPTIDE
<222> LOCATION: (1)..(11)
<223> OTHER INFORMATION: Amino acid sequence of peptide derived from
      bovine alpha-2 casein precursor.

<400> SEQUENCE: 4

Lys Thr Lys Val Ile Pro Tyr Val Arg Tyr Leu
1               5                   10

<210> SEQ ID NO 5
<211> LENGTH: 12
<212> TYPE: PRT
```

```
<213> ORGANISM: Bos taurus
<220> FEATURE:
<221> NAME/KEY: PEPTIDE
<222> LOCATION: (1)..(12)
<223> OTHER INFORMATION: Amino acid sequence of peptide derived from
      bovine alpha-2 casein precursor.

<400> SEQUENCE: 5

Pro Lys Thr Lys Val Ile Pro Tyr Val Arg Tyr Leu
1               5                   10

<210> SEQ ID NO 6
<211> LENGTH: 13
<212> TYPE: PRT
<213> ORGANISM: Bos taurus
<220> FEATURE:
<221> NAME/KEY: PEPTIDE
<222> LOCATION: (1)..(13)
<223> OTHER INFORMATION: Amino acid seuqence of peptide derived from
      bovine alpha-2 casein precursor.

<400> SEQUENCE: 6

Gln Pro Lys Thr Lys Val Ile Pro Tyr Val Arg Tyr Leu
1               5                   10

<210> SEQ ID NO 7
<211> LENGTH: 19
<212> TYPE: PRT
<213> ORGANISM: Bos taurus
<220> FEATURE:
<221> NAME/KEY: PEPTIDE
<222> LOCATION: (1)..(19)
<223> OTHER INFORMATION: Amino acid sequence of peptide derived from
      bovine alpha-S2 casein precursor.

<400> SEQUENCE: 7

Ala Met Lys Pro Trp Ile Gln Pro Lys Thr Lys Val Ile Pro Tyr Val
1               5                   10                  15

Arg Tyr Leu

<210> SEQ ID NO 8
<211> LENGTH: 26
<212> TYPE: PRT
<213> ORGANISM: Bos taurus
<220> FEATURE:
<221> NAME/KEY: PEPTIDE
<222> LOCATION: (1)..(26)
<223> OTHER INFORMATION: Amino acid of peptide derived from bovine
      alpha-S2 casein precursor

<400> SEQUENCE: 8

Thr Val Tyr Gln His Gln Lys Ala Met Lys Pro Trp Ile Gln Pro Lys
1               5                   10                  15

Thr Lys Val Ile Pro Tyr Val Arg Tyr Leu
                20                  25

<210> SEQ ID NO 9
<211> LENGTH: 31
<212> TYPE: PRT
<213> ORGANISM: Bos taurus
<220> FEATURE:
<221> NAME/KEY: PEPTIDE
<222> LOCATION: (1)..(31)
<223> OTHER INFORMATION: Amino acid of peptide derived from bovine
      alpha-S2 casein precursor.

<400> SEQUENCE: 9

Pro Gln Tyr Leu Lys Thr Val Tyr Gln His Gln Lys Ala Met Lys Pro
```

```
                      -continued
1               5                   10                  15

Trp Ile Gln Pro Lys Thr Lys Val Ile Pro Tyr Val Arg Tyr Leu
            20                  25                  30

<210> SEQ ID NO 10
<211> LENGTH: 223
<212> TYPE: PRT
<213> ORGANISM: Capra hircus
<220> FEATURE:
<221> NAME/KEY: PROPEP
<222> LOCATION: (1)..(223)
<223> OTHER INFORMATION: Amino acid sequence of goat alpha-S2 casein
      precursor.

<400> SEQUENCE: 10

Met Lys Phe Phe Ile Phe Thr Cys Leu Leu Ala Val Ala Leu Ala Lys
1               5                   10                  15

His Lys Met Glu His Val Ser Ser Glu Glu Pro Ile Asn Ile Phe
            20                  25                  30

Gln Glu Ile Tyr Lys Gln Glu Lys Asn Met Ala Ile His Pro Arg Lys
        35                  40                  45

Glu Lys Leu Cys Thr Thr Ser Cys Glu Glu Val Arg Asn Ala Asn
50                  55                          60

Glu Glu Glu Tyr Ser Ile Arg Ser Ser Glu Glu Ser Ala Glu Val
65                      70                  75                  80

Ala Pro Glu Glu Ile Lys Ile Thr Val Asp Asp Lys His Tyr Gln Lys
                85                  90                  95

Ala Leu Asn Glu Ile Asn Gln Phe Tyr Gln Lys Phe Pro Gln Tyr Leu
            100                 105                 110

Gln Tyr Pro Tyr Gln Gly Pro Ile Val Leu Asn Pro Trp Asp Gln Val
        115                 120                 125

Lys Arg Asn Ala Gly Pro Phe Thr Pro Thr Val Asn Arg Glu Gln Leu
    130                 135                 140

Ser Thr Ser Glu Glu Asn Ser Lys Lys Thr Ile Asp Met Glu Ser Thr
145                 150                 155                 160

Glu Val Phe Thr Lys Lys Thr Lys Leu Thr Glu Glu Lys Asn Arg
                165                 170                 175

Leu Asn Phe Leu Lys Lys Ile Ser Gln Tyr Tyr Gln Lys Phe Ala Trp
            180                 185                 190

Pro Gln Tyr Leu Lys Thr Val Asp Gln His Gln Lys Ala Met Lys Pro
        195                 200                 205

Trp Thr Gln Pro Lys Thr Asn Ala Ile Pro Tyr Val Arg Tyr Leu
    210                 215                 220

<210> SEQ ID NO 11
<211> LENGTH: 223
<212> TYPE: PRT
<213> ORGANISM: Capra hircus
<220> FEATURE:
<221> NAME/KEY: DOMAIN
<222> LOCATION: (1)..(223)
<223> OTHER INFORMATION: Amino acid sequence of goat alpha-S2 casein E.

<400> SEQUENCE: 11

Met Lys Phe Phe Ile Phe Thr Cys Leu Leu Ala Val Ala Leu Ala Lys
1               5                   10                  15

His Lys Met Glu His Val Ser Ser Glu Glu Pro Ile Asn Ile Phe
            20                  25                  30

Gln Glu Ile Tyr Lys Gln Glu Lys Asn Met Ala Ile His Pro Arg Lys
```

-continued

```
            35                  40                  45
Glu Lys Leu Cys Thr Thr Ser Cys Glu Val Val Arg Asn Ala Asn
 50                  55                  60
Glu Glu Glu Tyr Ser Ile Arg Ser Ser Ser Glu Glu Ser Ala Lys Val
65                   70                  75                  80
Ala Pro Glu Glu Ile Lys Ile Thr Val Asp Asp Lys His Tyr Gln Lys
                 85                  90                  95
Ala Leu Asn Glu Ile Asn Gln Phe Tyr Gln Lys Phe Pro Gln Tyr Leu
                100                 105                 110
Gln Tyr Pro Tyr Gln Gly Pro Ile Val Leu Asn Pro Trp Asp Gln Val
                115                 120                 125
Lys Arg Asn Ala Gly Pro Phe Thr Pro Thr Val Asn Arg Glu Gln Leu
            130                 135                 140
Ser Thr Ser Glu Glu Asn Ser Lys Lys Thr Ile Asp Met Glu Ser Thr
145                 150                 155                 160
Glu Val Phe Thr Lys Lys Thr Lys Leu Thr Glu Glu Lys Asn Arg
                165                 170                 175
Leu Asn Phe Leu Lys Lys Ile Ser Gln Tyr Tyr Gln Lys Phe Ala Trp
            180                 185                 190
Pro Gln Tyr Leu Lys Thr Val Asp Gln His Gln Lys Ala Met Lys Pro
                195                 200                 205
Trp Thr Gln Pro Lys Thr Asn Ala Ile Pro Tyr Val Arg Tyr Leu
            210                 215                 220
```

<210> SEQ ID NO 12
<211> LENGTH: 223
<212> TYPE: PRT
<213> ORGANISM: Capra hircus
<220> FEATURE:
<221> NAME/KEY: DOMAIN
<222> LOCATION: (1)..(223)
<223> OTHER INFORMATION: Amino acid sequence of goat alpha-S2 casein C.

<400> SEQUENCE: 12

```
Met Lys Phe Phe Ile Phe Thr Cys Leu Leu Ala Val Ala Leu Ala Lys
1               5                  10                  15
His Lys Met Glu His Val Ser Ser Ser Glu Glu Pro Ile Asn Ile Phe
                20                  25                  30
Gln Glu Ile Tyr Lys Gln Glu Lys Asn Met Ala Ile His Pro Arg Lys
            35                  40                  45
Glu Lys Leu Cys Thr Thr Ser Cys Glu Glu Val Val Arg Asn Ala Asn
 50                  55                  60
Glu Glu Glu Tyr Ser Ile Arg Ser Ser Ser Glu Glu Ser Ala Glu Val
65                   70                  75                  80
Ala Pro Glu Glu Ile Lys Ile Thr Val Asp Asp Lys His Tyr Gln Lys
                 85                  90                  95
Ala Leu Asn Glu Ile Asn Gln Phe Tyr Gln Lys Phe Pro Gln Tyr Leu
                100                 105                 110
Gln Tyr Pro Tyr Gln Gly Pro Ile Val Leu Asn Pro Trp Asp Gln Val
                115                 120                 125
Lys Arg Asn Ala Gly Pro Phe Thr Pro Thr Val Asn Arg Glu Gln Leu
            130                 135                 140
Ser Thr Ser Glu Glu Asn Ser Lys Lys Thr Ile Asp Met Glu Ser Thr
145                 150                 155                 160
Glu Val Phe Thr Lys Lys Thr Lys Leu Thr Glu Glu Lys Asn Arg
                165                 170                 175
```

```
Leu Asn Phe Leu Lys Ile Ile Ser Gln Tyr Tyr Gln Lys Phe Ala Trp
            180                 185                 190

Pro Gln Tyr Leu Lys Thr Val Asp Gln His Gln Lys Ala Met Lys Pro
        195                 200                 205

Trp Thr Gln Pro Lys Thr Asn Ala Ile Pro Tyr Val Arg Tyr Leu
    210                 215                 220

<210> SEQ ID NO 13
<211> LENGTH: 179
<212> TYPE: PRT
<213> ORGANISM: Oryctolagus cuniculus
<220> FEATURE:
<221> NAME/KEY: PROPEP
<222> LOCATION: (1)..(179)
<223> OTHER INFORMATION: Amino acid sequence of rabbit alpha-S2 casein
      form b precursor from -15 to 167

<400> SEQUENCE: 13

Met Lys Phe Phe Ile Phe Thr Cys Leu Leu Ala Val Ala Leu Ala Lys
1               5                   10                  15

Pro Lys Ile Glu Gln Ser Ser Ser Glu Glu Thr Ile Ala Val Ser Gln
            20                  25                  30

Glu Val Ser Pro Asn Leu Glu Asn Ile Cys Ser Thr Ala Cys Glu Glu
        35                  40                  45

Pro Ile Lys Asn Ile Asn Glu Val Glu Tyr Val Glu Val Pro Thr Glu
    50                  55                  60

Ile Lys Asp Gln Glu Phe Tyr Gln Lys Val Asn Leu Leu Gln Tyr Leu
65                  70                  75                  80

Gln Ala Leu Tyr Gln Tyr Pro Thr Val Met Asp Pro Trp Thr Arg Ala
                85                  90                  95

Glu Thr Lys Ala Ile Pro Phe Ile Arg Thr Met Gln Tyr Lys Gln Glu
            100                 105                 110

Lys Asp Ala Thr Lys His Thr Ser Gln Lys Thr Glu Leu Thr Glu Glu
        115                 120                 125

Glu Lys Ala Phe Leu Lys Tyr Leu Asp Glu Met Lys Gln Tyr Tyr Gln
    130                 135                 140

Lys Phe Val Phe Pro Gln Tyr Leu Lys Asn Ala His Phe Gln Lys
145                 150                 155                 160

Thr Met Asn Pro Trp Asn His Val Lys Thr Ile Ile Tyr Gln Ser Val
                165                 170                 175

Pro Thr Leu

<210> SEQ ID NO 14
<211> LENGTH: 223
<212> TYPE: PRT
<213> ORGANISM: Ovis aries
<220> FEATURE:
<221> NAME/KEY: PROPEP
<222> LOCATION: (1)..(223)
<223> OTHER INFORMATION: Amino acid sequence of sheep alpha-S2 casein
      precursor.

<400> SEQUENCE: 14

Met Lys Phe Phe Ile Phe Thr Cys Leu Leu Ala Val Ala Leu Ala Lys
1               5                   10                  15

His Lys Met Glu His Val Ser Ser Ser Glu Glu Pro Ile Asn Ile Ser
            20                  25                  30

Gln Glu Ile Tyr Lys Gln Glu Lys Asn Met Ala Ile His Pro Arg Lys
        35                  40                  45
```

```
Glu Lys Leu Cys Thr Thr Ser Cys Glu Glu Val Val Arg Asn Ala Asp
             50                  55                  60

Glu Glu Glu Tyr Ser Ile Arg Ser Ser Glu Glu Ser Ala Glu Val
 65                  70                  75                  80

Ala Pro Glu Glu Val Lys Ile Thr Val Asp Asp Lys His Tyr Gln Lys
                     85                  90                  95

Ala Leu Asn Glu Ile Asn Gln Phe Tyr Gln Lys Phe Pro Gln Tyr Leu
                100                 105                 110

Gln Tyr Leu Tyr Gln Gly Pro Ile Val Leu Asn Pro Trp Asp Gln Val
            115                 120                 125

Lys Arg Asn Ala Gly Pro Phe Thr Pro Thr Val Asn Arg Glu Gln Leu
        130                 135                 140

Ser Thr Ser Glu Glu Asn Ser Lys Lys Thr Ile Asp Met Glu Ser Thr
145                 150                 155                 160

Glu Val Phe Thr Lys Lys Thr Lys Leu Thr Glu Glu Lys Asn Arg
                165                 170                 175

Leu Asn Phe Leu Lys Lys Ile Ser Gln Tyr Tyr Gln Lys Phe Ala Trp
                180                 185                 190

Pro Gln Tyr Leu Lys Thr Val Asp Gln His Gln Lys Ala Met Lys Pro
            195                 200                 205

Trp Thr Gln Pro Lys Thr Asn Ala Ile Pro Tyr Val Arg Tyr Leu
            210                 215                 220

<210> SEQ ID NO 15
<211> LENGTH: 235
<212> TYPE: PRT
<213> ORGANISM: Sus domesticus
<220> FEATURE:
<221> NAME/KEY: PROPEP
<222> LOCATION: (1)..(235)
<223> OTHER INFORMATION: Amino acid sequence of pig alpha-S2 casein
      precursor.

<400> SEQUENCE: 15

Met Lys Phe Phe Ile Phe Thr Cys Leu Leu Ala Val Ala Phe Ala Lys
  1               5                  10                  15

His Glu Met Glu His Val Ser Ser Ser Glu Glu Ser Ile Asn Ile Ser
                 20                  25                  30

Gln Glu Lys Tyr Lys Gln Glu Lys Asn Val Ile Asn His Pro Ser Lys
             35                  40                  45

Glu Asp Ile Cys Ala Thr Ser Cys Glu Glu Ala Val Arg Asn Ile Lys
         50                  55                  60

Glu Val Gly Tyr Ala Ser Ser Ser Ser Glu Glu Ser Val Asp Ile
 65                  70                  75                  80

Pro Ala Glu Asn Val Lys Val Thr Val Glu Asp Lys His Tyr Leu Lys
                     85                  90                  95

Gln Leu Glu Lys Ile Ser Gln Phe Tyr Gln Lys Phe Pro Gln Tyr Leu
                100                 105                 110

Gln Ala Leu Tyr Gln Ala Gln Ile Val Met Asn Pro Trp Asp Gln Thr
            115                 120                 125

Lys Thr Ser Ala Tyr Pro Phe Ile Pro Thr Val Ile Gln Ser Gly Glu
        130                 135                 140

Glu Leu Ser Thr Ser Glu Glu Pro Val Ser Ser Gln Glu Glu Asn
145                 150                 155                 160

Thr Lys Thr Val Asp Met Glu Ser Met Glu Glu Phe Thr Lys Lys Thr
                165                 170                 175
```

-continued

Glu Leu Thr Glu Glu Glu Lys Asn Arg Ile Lys Phe Leu Asn Lys Ile
            180                 185                 190

Lys Gln Tyr Tyr Gln Lys Phe Thr Trp Pro Gln Tyr Ile Lys Thr Val
        195                 200                 205

His Gln Lys Gln Lys Ala Met Lys Pro Trp Asn His Ile Lys Thr Asn
    210                 215                 220

Ser Tyr Gln Ile Ile Pro Asn Leu Arg Tyr Phe
225                 230                 235

<210> SEQ ID NO 16
<211> LENGTH: 5
<212> TYPE: PRT
<213> ORGANISM: Bos taurus
<220> FEATURE:
<221> NAME/KEY: PEPTIDE
<222> LOCATION: (1)..(5)
<223> OTHER INFORMATION: Amino acid of peptide derived from bovine
      alpha-S2 casein precursor

<400> SEQUENCE: 16

Lys Val Ile Pro Tyr
1               5

<210> SEQ ID NO 17
<211> LENGTH: 6
<212> TYPE: PRT
<213> ORGANISM: Bos taurus
<220> FEATURE:
<221> NAME/KEY: PEPTIDE
<222> LOCATION: (1)..(6)
<223> OTHER INFORMATION: Amino acid of peptide derived from bovine
      alpha-S2 casein precursor

<400> SEQUENCE: 17

Thr Lys Val Ile Pro Tyr
1               5

<210> SEQ ID NO 18
<211> LENGTH: 7
<212> TYPE: PRT
<213> ORGANISM: Bos taurus
<220> FEATURE:
<221> NAME/KEY: PEPTIDE
<222> LOCATION: (1)..(7)
<223> OTHER INFORMATION: Amino acid of peptide derived from bovine
      alpha-S2 casein precursor

<400> SEQUENCE: 18

Lys Thr Lys Val Ile Pro Tyr
1               5

<210> SEQ ID NO 19
<211> LENGTH: 8
<212> TYPE: PRT
<213> ORGANISM: Bos taurus
<220> FEATURE:
<221> NAME/KEY: PEPTIDE
<222> LOCATION: (1)..(8)
<223> OTHER INFORMATION: Amino acid of peptide derived from bovine
      alpha-S2 casein precursor

<400> SEQUENCE: 19

Pro Lys Thr Lys Val Ile Pro Tyr
1               5

<210> SEQ ID NO 20

```
<211> LENGTH: 9
<212> TYPE: PRT
<213> ORGANISM: Bos taurus
<220> FEATURE:
<221> NAME/KEY: PEPTIDE
<222> LOCATION: (1)..(9)
<223> OTHER INFORMATION: Amino acid of peptide derived from bovine
      alpha-S2 casein precursor

<400> SEQUENCE: 20

Gln Pro Lys Thr Lys Val Ile Pro Tyr
1               5

<210> SEQ ID NO 21
<211> LENGTH: 15
<212> TYPE: PRT
<213> ORGANISM: Bos taurus
<220> FEATURE:
<221> NAME/KEY: PEPTIDE
<222> LOCATION: (1)..(15)
<223> OTHER INFORMATION: Amino acid of peptide derived from bovine
      alpha-S2 casein precursor

<400> SEQUENCE: 21

Ala Met Lys Pro Trp Ile Gln Pro Lys Thr Lys Val Ile Pro Tyr
1               5                   10                  15

<210> SEQ ID NO 22
<211> LENGTH: 22
<212> TYPE: PRT
<213> ORGANISM: Bos taurus
<220> FEATURE:
<221> NAME/KEY: PEPTIDE
<222> LOCATION: (1)..(22)
<223> OTHER INFORMATION: Amino acid of peptide derived from bovine
      alpha-S2 casein precursor

<400> SEQUENCE: 22

Thr Val Tyr Gln His Gln Lys Ala Met Lys Pro Trp Ile Gln Pro Lys
1               5                   10                  15

Thr Lys Val Ile Pro Tyr
            20

<210> SEQ ID NO 23
<211> LENGTH: 27
<212> TYPE: PRT
<213> ORGANISM: Bos taurus
<220> FEATURE:
<221> NAME/KEY: PEPTIDE
<222> LOCATION: (1)..(27)
<223> OTHER INFORMATION: Amino acid sequence of bovine alpha-S2 casein
      precursor

<400> SEQUENCE: 23

Pro Gln Tyr Leu Lys Thr Val Tyr Gln His Gln Lys Ala Met Lys Pro
1               5                   10                  15

Trp Ile Gln Pro Lys Thr Lys Val Ile Pro Tyr
            20                  25

<210> SEQ ID NO 24
<211> LENGTH: 4
<212> TYPE: PRT
<213> ORGANISM: Bos taurus
<220> FEATURE:
```

-continued

```
<221> NAME/KEY: PEPTIDE
<222> LOCATION: (1)..(4)
<223> OTHER INFORMATION: Amino acid of peptide derived from bovine
      alpha-S2 casein precursor

<400> SEQUENCE: 24

Val Arg Tyr Leu
1
```